United States Patent
Glad et al.

(10) Patent No.: US 8,470,148 B2
(45) Date of Patent: Jun. 25, 2013

(54) METHOD FOR SAMPLE APPLICATION

(75) Inventors: Gunnar Glad, Uppsala (SE); Nils Norrman, Uppsala (SE); Susanna Lindman, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 0 days.

(21) Appl. No.: 12/812,466

(22) PCT Filed: Jan. 19, 2009

(86) PCT No.: PCT/SE2009/000019
§ 371 (c)(1),
(2), (4) Date: Jul. 12, 2010

(87) PCT Pub. No.: WO2009/091320
PCT Pub. Date: Jul. 23, 2009

(65) Prior Publication Data
US 2010/0282610 A1    Nov. 11, 2010

(30) Foreign Application Priority Data
Jan. 17, 2008 (SE) ........................... 0800111

(51) Int. Cl.
*G01N 27/447* (2006.01)
(52) U.S. Cl.
USPC ............................ 204/450; 435/176; 436/526

(58) Field of Classification Search
USPC .................. 204/450–470; 530/412; 435/176, 435/288.6; 436/524–526
See application file for complete search history.

(56) References Cited

U.S. PATENT DOCUMENTS

| | | | |
|---|---|---|---|
| 3,839,183 A | 10/1974 | Klein et al. | |
| 3,855,846 A | 12/1974 | Forget et al. | |
| 5,395,498 A | 3/1995 | Gombinslky et al. | |
| 5,405,516 A | 4/1995 | Bellon | |
| 5,683,915 A | 11/1997 | Black et al. | |
| 6,649,419 B1 | 11/2003 | Anderson | |
| 2004/0023273 A1 | 2/2004 | Puget et al. | |
| 2005/0155861 A1* | 7/2005 | Guzman | 204/451 |
| 2006/0144706 A1 | 7/2006 | Adourian et al. | |

FOREIGN PATENT DOCUMENTS
EP    1 662 256    5/2006

* cited by examiner

Primary Examiner — J. Christopher Ball

(57) ABSTRACT

The present invention relates to a method for sample application and separation. More closely, the invention relates to convenient direct loading of a biomolecule sample via magnetic beads to, for example, a gel before electrophoresis. In this way, the invention combines elution and application steps with minimal losses of sample. Thus, the invention relates to a method for sample application of biomolecules on a separation media, comprising the following steps: a) obtaining said biomolecules from a sample by magnetic beads; b) applying the magnetic beads with the biomolecules to a separation medium; c) releasing the biomolecules into the separation media, and d) separation of the biomolecules from each other in the separation medium.

10 Claims, 2 Drawing Sheets

METHOD FOR SAMPLE APPLICATION

CROSS-REFERENCE TO RELATED APPLICATIONS

This application is a filing under 35 U.S.C. §371 and claims priority to international patent application number PCT/SE2009/000019 filed Jan. 19, 2009, published on Jul. 23, 2009, as WO 2009/091320, which claims priority to patent application number 0800111-7 filed in Sweden on Jan. 17, 2008.

FIELD OF THE INVENTION

The present invention relates to a method for sample application on electrophoretic gels. More closely, the invention relates to convenient direct loading of a biomolecule sample via magnetic beads to the gel before electrophoresis. In this way, the invention combines elution and application steps with minimal losses of sample.

BACKGROUND OF THE INVENTION

The isolation of biomolecules, such as proteins and peptides, has become of an increased interest during the past years. Some biomolecules need to be isolated as a last step of a biotechnological method for the production thereof, for example in the preparation of protein-based pharmaceutical compounds. Similarly there is also a need to separate biomolecules for analytical purposes in order to be able to quantitate and identify the proteins and/or peptides present in a sample. Electrophoretic methods are commonly used in the separation step.

Loading of samples onto electrophoretic gels may be done in different ways. The most common way is to provide the sample solution with a heavy medium and load the mixture in the bottom of a preformed well in the electrophoretic gel or by applying the sample solution onto paper strips placed on an vertical electrophoretic gel. Other ways of sample loading, used in for example isoelectric focusing, is cup loading or paper bridge loading.

Many analytical and preparative electrophoretic techniques are sensitive for sample contents and the results are often affected in a negative way by unwanted high abundant proteins. The bad influence can have several origins, such as sample preparation and/or sample application techniques.

It would be desirable to have control of both the sample content by for example specific enrichment and the sample application, preferably at the same time, which would increase the quality as well as the reproducibility of the results. It would be convenient to combine the sample preparation and application to have only one sample preparation-application step and this will also reduce losses of sample.

Magnetic beads are a convenient format which enables enrichment/capture from a large sample volume which is concentrated to a small amount before analysis.

SUMMARY OF THE INVENTION

This present invention combines biomolecule enrichment with sample application, especially for electrophoresis, by using magnetic beads. Combining the elution step with the sample application step for a downstream gel analysis, for example a SDS-PAGE gel, gives a high level of convenience. Another benefit is that losses are decreased when the sample has to be transferred multiple times.

Thus, the present invention relates to a Method for sample application of biomolecules on a separation media, comprising the following steps: a) obtaining said biomolecules from a sample by magnetic beads; b) applying the magnetic beads with the biomolecules to a separation medium; c) releasing the biomolecules into the separation media, and d) separation of the biomolecules from each other in the separation medium. The biomolecules may be attached to the surface of the magnetic beads and/or be attached integrated in the magnetic beads.

The biomolecule may be any biomolecule or substance but is preferably a protein.

Preferably the magnetic beads are functionalized with ligand(s) selected from ion exchange, hydrophobic interaction, affinity, depending on the desired biomolecules. Unmodified magnetic beads, i.e. not functionalized beads, could be used as a sample applicator or sample carrier for transfer to the separation media, where the bead volume defines the sample volume.

Preferably, the separation medium is an electrophoretic gel or an iso-electric focusing strip.

In the method, the biomolecules may be electroforetically separated while the magnetic beads are present on the gel or by first removing the magnetic beads.

DETAILED DESCRIPTION OF THE INVENTION

Figure 1:
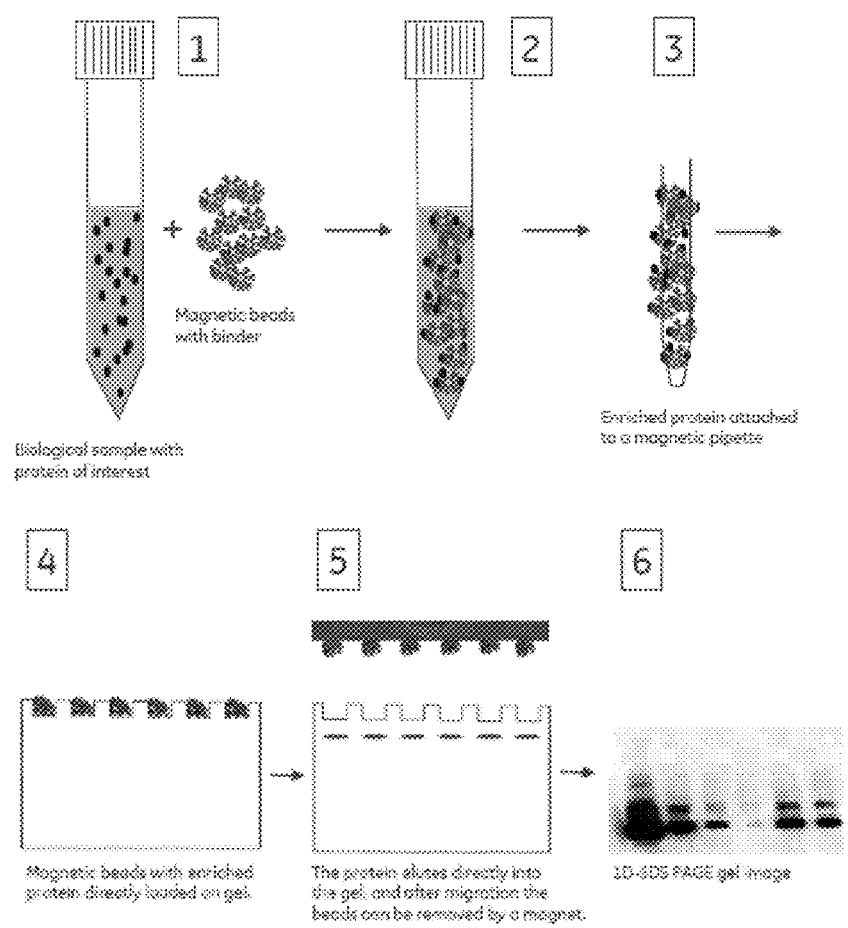
FIG. 1 shows a typical workflow for practicing the method according to the present invention.

With reference to FIG. 1, the first step in the method of the invention comprises addition of magnetic beads to a biological sample containing different biomolecules, in this case present in a test tube. The magnetic beads are provided with a binder, such as an affinity ligand for the biomolecule of interest. A PICKPEN® may be used to transfer the magnetic particles to the tubes. This gives a handy small-scale size which is very suitable for direct loading on gel.

In a second step, the biomolecules of interest bind to the binder on the magnetic beads.

In a third step, the magnetic beads with attached biomolecules are captured from the tube with the aid of a magnetic force. The capture may be done manually as described in the examples below, or done automatically with either one or dual (upper/lower) magnetic instrument.

In a fourth step, the magnetic beads with attached biomolecules are applied to a separation medium, such as an electrophoretic gel, as a sample applicator in an automatic electrophoresis system.

By using a dual magnet system the lower magnet will be used for localisation of the sample and beads in discrete spots.

In a fifth step, the biomolecules are eluted into the gel by either the running buffer conditions and/or the electric current.

All these steps could be performed in an integrated system covering the complete workflow in sample preparation.

The magnetic beads can either remain on gel during the electrophoresis run or optionally be removed after approximately 10-15 min when the sample has entered the gel. It was unexpected that it was not needed to remove the magnetic beads from the gel. In fact, the magnetic beads did not essentially influence the result of the electrophoresis at all.

There is also a possibility that the sample applicator can be magnetic so the beads stay attached to it when the sample is eluted into the gel bed.

In a sixth step, the biomolecules are detected on the gel.

Control of both the sample content and the sample application increases the quality as well as the reproducibility of the results of the electrophoresis.

The invention will be more closely described below in connection with some non-limiting examples.

Magnetite dissolved in agarose solution is emulsified with toluene to a suitable particle size. The different ligands are coupled with standard coupling chemistries.

Agarose (1.8 g) was dissolved in water (30 mL) by heating at 95° C. for 60 min Iron oxide powder (6.0 g) was added to the agarose solution. The suspension was cooled to 60° C. and added to toluene (100 ml) and Prisorine 3700 (0.67 g) in an emulsification vessel. The emulsification vessel was equipped with a 40 mm turbine stirrer. The speed of the stirrer was kept at 300 rpm and the temperature was kept at 60° C. After approximately 5 minutes the speed of the stirrer was increased, maintaining the temperature at 60° C. until desired particle size is obtained.

Thereafter the emulsion was cooled and the beads were allowed to gel. The beads were washed with ethanol and water and enriched using a magnet. From the procedure magnetic particles were obtained, containing iron oxide powder.

The outer agarose layer is also suited for further derivatisation with any desirable ligand that fulfils the needs for the intended application. Such applications can be protein, nucleic acid, virus or cell separation/concentration or any diagnostic application. The magnetic beads of the invention may be used for column chromatography, chromatography in fluidised beds, batch-wise procedures, immunoprecipitations, protein arrays on solid phase or in solution, high throughput analysis, cell-cultivating purposes etc.

EXAMPLES

Below the present invention will be disclosed by way of examples, which are intended solely for illustrative purposes and should not be construed as limiting the present invention as defined in the appended claims. All references mentioned below or elsewhere in the present application are hereby included by reference.

Experimental Example 1

500 µL of a 20% slurry of magnetic agarose beads functionalised with a Q ligand (quaternary amine $-N^+(CH_3)_3$, a strong anion exchanger) are incubated for 1 h with 5 ml to protein sample mix consisting of Lysozyme 1 mg/ml, Ribonuclease A 1 mg/ml, Bovine serum albumine 1 mg/ml and IgG 1 mg/ml in 50 mM sodiumphosphate buffer, pH 7.0 (total protein concentration of 4 mg/ml).

After the incubation the magnetic beads are transferred to a tube with 50 mM sodiumphosphate buffer, pH 7.0 for washing.

1 µl of the beads are then loaded into the well of a vertical SDS-PAGE electrophoresis gel with or without sample loading buffer containing SDS and the proteins are eluted directly into the gel during the electrophoresis.

Experimental Example 2

500 µL of a 20% slurry of magnetic agarose beads functionalised with a S ligand ($-SO_3^-$, strong cation exchanger) are incubated for 1 h with 5 ml protein sample mix consisting of Lysozyme 1 mg/ml, Ribonuclease A 1 mg/ml, Bovine serum albumine 1 mg/ml and IgG 1 mg/ml in 50 mM sodiumphosphate buffer, pH 7.0 (total protein concentration of 4 mg/ml).

After the incubation the magnetic beads are transferred to a tube with 50 mM sodiumphosphate buffer, pH 7.0 for washing.

1 µl of the beads are then loaded onto an electrophoresis gel with or without sample loading buffer containing SDS and the proteins are eluted directly into the gel during the electrophoresis.

Results

Figure 2:
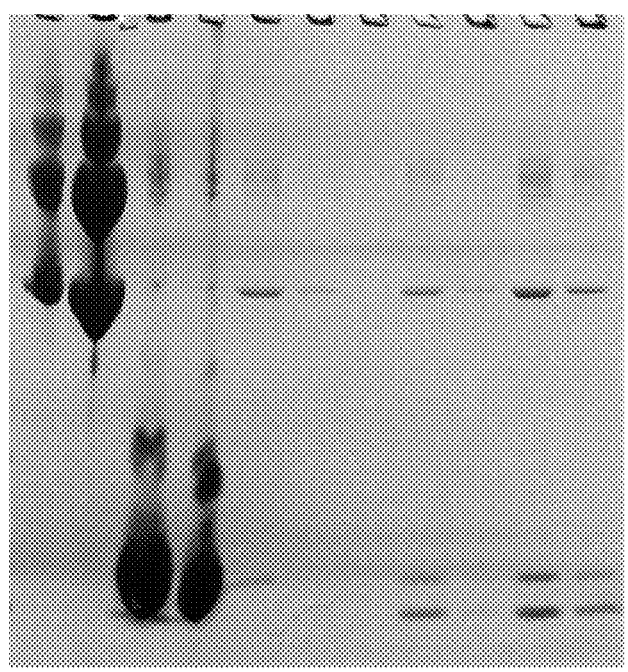
FIG. 2 shows a stained electrophoresis gel obtained after sample application by using magnetic beads according to the invention.

The results from the electrophoresis are shown in FIG. 2 which shows a Coomassie—stained vertical SDS-PAGE gel. The lanes contained the following:
1. Magnetic beads with Q ligands+sample without loading buffer
2. Magnetic beads with Q ligands+sample with loading buffer
3. Magnetic beads with S ligands+sample with loading buffer
4. Magnetic beads with S ligands+sample without loading buffer
5. Remaining sample solution after depletion with magnetic beads with S ligands
6. Remaining sample solution after depletion with magnetic beads with Q ligands
7. Original sample (protein conc. 4 mg/ml) IgG:BSA:RNAse:Lys (1:1:1:1)

In lane 7, 1 µl of the sample was applied with a total protein concentration of 4 mg/ml consisting of IgG, BSA, RNAse and lysozyme (1:1:1:1).

In lanes 1-4, 1 µl of magnetic beads was applied with or without loading buffer, excluding any pre-elution step.

As shown from the stained gel, the beads have high capacity therefore the bands are overloaded. It seems that it works equally well to exclude the standard loading buffer as they display same spot pattern. The magnetic beads with Q ligands has enriched IgG (pI 5.8-7.3) and BSA (pI 4.7-5.2) and the magnetic beads with S ligands has enriched RNAse (pI 9.3) and lysozyme (pI 9.4) at the experimental binding conditions (50 mM sodium phosphate, pH 7.0).

In lanes 5 and 6, 1 µl of each remaining sample solution (after removal of the incubated magnetic beads) is applied. As appears from the figure, very little protein is left.

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

What is claimed is:

1. A method for sample application of biomolecules on a separation media, comprising the following steps:
    a) separating said biomolecules from a sample by magnetic beads, wherein the magnetic beads are associated with ligands specific for said biomolecule and wherein the beads comprise magnetite particles with an outer layer of agarose;
    b) applying the magnetic beads with the biomolecules in contact with or directly onto a separation medium;
    c) releasing the biomolecules into the separation media; and
    d) electrophoretically separating the biomolecules from each other in the separation medium.

2. The method of claim 1, wherein the ligands are selected from the group consisting of ion exchange, hydrophobic interaction, affinity, chelating, ligands for reverse phase chromatography (RPC) or multimodal ligands or a combination thereof.

3. The method of claim 2, wherein the ligands are anion exchange ligands.

4. The method of claim 2, wherein the ligands are cation exchange ligands.

5. The method of claim 1, wherein the magnetic beads are used as a sample applicator or sample carrier, where the bead volume defines the sample volume.

6. The method of claim 1, wherein the biomolecules are electrophoretically separated while the magnetic beads are present on the gel.

7. The method of claim 1, wherein the magnetic beads are removed from the gel.

8. The method of claim 1, wherein the biomolecules are proteins.

9. The method of claim 1, wherein the separation medium is an electrophoretic gel or an iso-electric focusing strip.

10. The method of claim 1, wherein the agarose is derivatised with ligands specific for said biomolecules.

* * * * *